United States Patent
Nguyen et al.

(10) Patent No.: US 9,637,575 B2
(45) Date of Patent: May 2, 2017

(54) CATALYST SYSTEM, OLEFIN POLYMERIZATION CATALYST COMPONENTS COMPRISING AT LEAST AN INTERNAL ELECTRON DONOR COMPOUND, AND METHODS OF MAKING AND USING THE SAME

(71) Applicant: W.R. Grace & Co.-Conn., Columbia, MD (US)

(72) Inventors: Binh Thanh Nguyen, League City, TX (US); Jonas Alves Fernandes, Triunfo (BR)

(73) Assignee: W. R. GRACE & CO. -CONN., Columbia, MD (US)

( * ) Notice: Subject to any disclaimer, the term of this patent is extended or adjusted under 35 U.S.C. 154(b) by 41 days.

(21) Appl. No.: 14/588,379

(22) Filed: Dec. 31, 2014

(65) Prior Publication Data

US 2016/0185886 A1    Jun. 30, 2016

(51) Int. Cl.
C07D 311/84    (2006.01)
C08F 110/06    (2006.01)

(52) U.S. Cl.
CPC .......... *C08F 110/06* (2013.01); *C07D 311/84* (2013.01)

(58) Field of Classification Search
None
See application file for complete search history.

(56) References Cited

U.S. PATENT DOCUMENTS 5,998,496 A    12/1999    Hassoon et al.
7,049,377 B1    5/2006    Morini et al.
(Continued)

FOREIGN PATENT DOCUMENTS

| CN | 104109212 A | * 10/2014 |
| WO | WO-00/04011 | 1/2000 |
| WO | WO-2009/129004 | 10/2009 |
| WO | WO-2012/155022 | 11/2012 |

OTHER PUBLICATIONS

Grinev et al., Quinones. XXIII. Condensation of p-benzoquinone and 2,3-dichloroquinone with acetoacetic ester and its analogs, Zhurnal Obshchei Khimii (1958), 28, 1856-64.
(Continued)

*Primary Examiner* — Catherine S Branch
(74) *Attorney, Agent, or Firm* — Foley & Lardner LLP

(57) ABSTRACT

An olefin polymerization catalyst component comprising an internal electron donor compound shown in formula (I) below is provided in this disclosure:

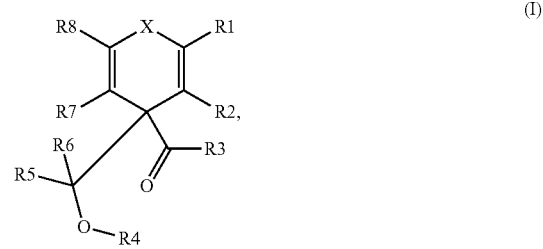

(I)

wherein X is O, S, $NR^a$, $PR^b$, or $POOR^c$,
$R^a$ is independently hydrogen, halogen, carbonyl hydrocarbon, linear or branched unsaturated or saturated alkyl hydrocarbon, cyclic, aromatic, or aliphatic hydrocarbon,
$R^b$ is independently hydrogen, halogen, carbonyl hydrocarbon, linear or branched unsaturated or saturated alkyl hydrocarbon, linear or branched unsaturated or saturated alkoxy hydrocarbon, cyclic, aromatic, or aliphatic hydrocarbon,
$R^c$ is independently hydrogen, carbonyl hydrocarbon, linear or branched unsaturated or saturated alkyl hydrocarbon, cyclic, aromatic, or aliphatic hydrocarbon,
(Continued)

R1-R8 are identical or different hydrogen, halogen, linear or branched unsaturated or saturated $C_1$-$C_{30}$ alkyl, alone or in combination with $C_5$-$C_{30}$ substituted or unsubstituted 5-or 6-membered aliphatic or aromatic hydrocarbon rings, each of $R^a$, $R^b$, $R^c$, and/or R1-R8 are optionally substituted with halogen.

22 Claims, 3 Drawing Sheets

(56) References Cited

U.S. PATENT DOCUMENTS

| 7,388,061 B2 | 6/2008 | Gao et al. |
| 8,227,370 B2 | 7/2012 | Chang |
| 8,318,626 B2 | 11/2012 | Chang |

OTHER PUBLICATIONS

Wang et al., Manganese(III) acetate initiated oxidative free radical reaction between 2-aryloxy-1,4-naphthoquinones and dialkyl malonates, Heterocycles (1999), 50(1), 489-497.

Akagi et al., Syntheses of 9-substituted derivatives of xanthene. II. 9,9-Xanthenedicarboxylic acid and 9-aryl-9-xanthenecarboxylic acids, Yakugaku Zasshi (1954), 74, 610-14.

Kasztreiner et al., Methadone analogs containing the xanthene skeleton. II Preparation of the isomeric 9-(morpholino) propyl-9-propionylxanthenes, Acta Chimica Academiae Scientiarum Hungaricae (1963), 38(2), 137-43.

Martell et al., Esters of Bicyclic Arninoalcohols as Potential Anticholinergics III—Synthesis of Some Isomeric Hydroxy-1-azabicyclonanes and Certain of Their Esters, J. of Pharm. Sci., (1963), 52(4), 331-336.

Kong et al., Synthesis of methyl 9-hydroxy-9-xanthenecarboxylate and intermediate, Huaxue Tongbao (2009), 72(6), 569-572.

Ueda, The Rearrangement of 10-Bromo-10,11-dihydrodibenzo[b,f]thiepin-11-one and Related Compounds in an Alkaline Solution, Bulletin of the Chemical Society of Japan, vol. 48(8), 2306-2309 (1975).

Kimoto, Friedel-Crafts reaction of diphenyl ether derivatives. X. Formation of 9-hydroxy-9-xanthenecarboxylates, Yakugaku Zasshi (1955), 75, 509-11.

International Search Report and Written Opinion of the International Searching Authority received in Application No. PCT/US2015/068259, mailed Mar. 31, 2016, 11 pages.

* cited by examiner

CATALYST SYSTEM, OLEFIN POLYMERIZATION CATALYST COMPONENTS COMPRISING AT LEAST AN INTERNAL ELECTRON DONOR COMPOUND, AND METHODS OF MAKING AND USING THE SAME

TECHNICAL FIELD

This application relates to a catalyst system including an olefin polymerization catalyst component for use in olefin polymerization. The olefin polymerization catalyst component comprises internal electron donor compounds described in this application. This application further relates to methods of making the olefin polymerization catalyst components and the catalyst systems, and methods of polymerizing or copolymerizing alpha-olefins using the catalyst systems.

BACKGROUND

Polyolefins are a class of polymers derived from simple olefins. Most commonly, methods of making polyolefins involve the use of Ziegler-Natta polymerization catalysts. These Ziegler-Natta polymerization catalysts polymerize vinyl monomers using a transition metal halide to provide a polymer with an isotactic stereochemical configuration.

A type of Ziegler-Natta catalyst system that is traditionally used for the polymerization or copolymerization of olefins comprises $TiCl_3$ based catalysts components obtained, for example, by the reduction of $TiCl_4$ with Al-alkyls, used in combination with Al-compounds such as diethylaluminum chloride (DEAC). These catalysts are characterized by a very low activity which results in the presence of large amounts of catalytic residues in the polymers.

During the past 30 years, numerous Ziegler-Natta catalysts have been developed which can afford improved activity in olefin polymerization reactions.

However, there still remains a need for development of new internal electron donor compounds that can provide highly desirable activity in olefin polymerization reactions and increased contents of crystalline isotactic fractions in the olefinic polymers they produce.

SUMMARY

According to one embodiment, an olefin polymerization catalyst component comprising an internal electron donor compound shown in formula (I) below is provided:

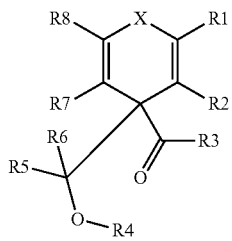

wherein X is O, S, $NR^a$, $PR^b$, or $POOR^c$ wherein $R^a$ is independently hydrogen or halogen, or wherein $R^a$ is independently carbonyl hydrocarbon, linear or branched unsaturated or saturated alkyl hydrocarbon, cyclic, aromatic, or aliphatic hydrocarbon, each of which are optionally substituted with halogen, wherein $R^b$ is independently hydrogen or halogen, or wherein $R^b$ is independently carbonyl hydrocarbon, linear or branched unsaturated or saturated alkyl hydrocarbon, linear or branched unsaturated or saturated alkoxy hydrocarbon, cyclic, aromatic, or aliphatic hydrocarbon, each of which are optionally substituted with halogen, wherein $R^c$ is hydrogen, or wherein $R^c$ is carbonyl hydrocarbon, linear or branched unsaturated or saturated alkyl hydrocarbon, cyclic, aromatic, or aliphatic hydrocarbon, each of which are optionally substituted with halogen, R1-R8 are identical or different hydrogen or halogen, or R1-R8 are identical or different linear or branched unsaturated or saturated $C_1$-$C_{30}$ alkyl, alone or in combination with $C_5$-$C_{30}$ substituted or unsubstituted 5- or 6-membered aliphatic or aromatic hydrocarbon rings, each of which are optionally substituted with halogen.

According to another embodiment, a catalyst system for use in olefinic polymerization comprising: the olefin polymerization catalyst component described hereinabove; an organoaluminum compound; and an organosilicon compound is provided.

According to yet another embodiment, a process of polymerizing or copolymerizing an olefin monomer comprising: (i) providing the catalyst system described hereinabove; (ii) polymerizing or copolymerizing the olefin monomer in the presence of the catalyst system to form a polymer or a copolymer; and (iii) recovering the polymer or the copolymer is provided.

According to a further embodiment, a catalyst system for polymerization of an olefin comprising a catalyst component comprising an internal electron donor compound shown in formula (I) below is provided:

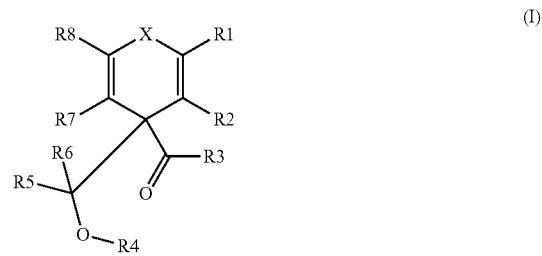

wherein X is O, S, $NR^a$, $PR^b$, or $POOR^c$ wherein $R^a$ is independently hydrogen or halogen, or wherein $R^a$ is independently carbonyl hydrocarbon, linear or branched unsaturated or saturated alkyl hydrocarbon, cyclic, aromatic, or aliphatic hydrocarbon, each of which are optionally substituted with halogen, wherein $R^b$ is independently hydrogen or halogen, or wherein $R^b$ is independently carbonyl hydrocarbon, linear or branched unsaturated or saturated alkyl hydrocarbon, linear or branched unsaturated or saturated alkoxy hydrocarbon, cyclic, aromatic, or aliphatic hydrocarbon, each of which are optionally substituted with halogen, wherein $R^c$ is hydrogen, or wherein $R^c$ is carbonyl hydrocarbon, linear or branched unsaturated or saturated alkyl hydrocarbon, cyclic, aromatic, or aliphatic hydrocarbon, each of which are optionally substituted with halogen, R1-R8 are identical or different hydrogen or halogen, or R1-R8 are identical or different linear or branched unsaturated or saturated $C_1$-$C_{30}$ alkyl, alone or in combination with $C_5$-$C_{30}$ substituted or unsubstituted 5- or 6-membered aliphatic or aromatic hydrocarbon rings, each of which are optionally substituted with halogen.

DETAILED DESCRIPTION

Figure 1:
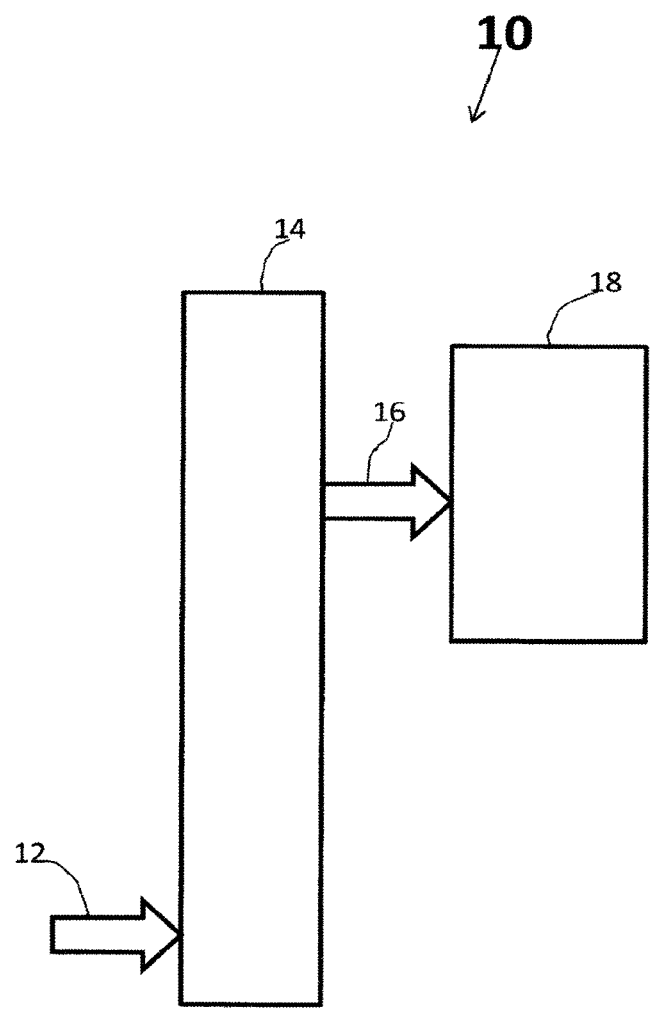
FIG. 1 is a high level schematic diagram of an olefin polymerization system in accordance with one embodiment of this application.

The terms "about" or "approximately" when used herein and associated with a numeric value refer to that numeric value plus or minus 10%, preferably plus or minus 5%, more preferably plus or minus 2%, most preferably plus or minus 1%.

As used herein, the term "application", "disclosure", and "specification" are interchangeable and refer to the various embodiments of the invention described herein.

According to one embodiment, an olefin polymerization catalyst component comprising an internal electron donor compound shown in formula (I) below is provided:

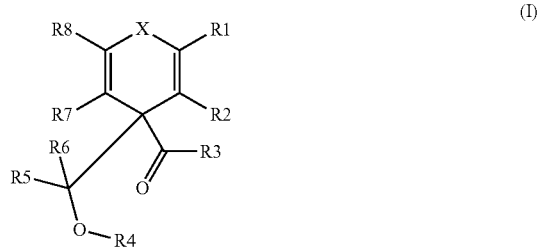

wherein
X is O, S, $NR^a$, $PR^b$, or $POOR^c$
wherein $R^a$ is independently hydrogen or halogen, or
  wherein $R^a$ is independently carbonyl hydrocarbon, linear or branched unsaturated or saturated alkyl hydrocarbon, cyclic, aromatic, or aliphatic hydrocarbon, each of which are optionally substituted with halogen,
wherein $R^b$ is independently hydrogen or halogen, or
  wherein $R^b$ is independently carbonyl hydrocarbon, linear or branched unsaturated or saturated alkyl hydrocarbon, linear or branched unsaturated or saturated alkoxy hydrocarbon, cyclic, aromatic, or aliphatic hydrocarbon, each of which are optionally substituted with halogen,
wherein $R^c$ is hydrogen, or wherein $R^c$ is carbonyl hydrocarbon, linear or branched unsaturated or saturated alkyl hydrocarbon, cyclic, aromatic, or aliphatic hydrocarbon, each of which are optionally substituted with halogen,
R1-R8 are identical or different hydrogen or halogen, or
R1-R8 are identical or different linear or branched unsaturated or saturated $C_1$-$C_{30}$ alkyl, alone or in combination with $C_5$-$C_{30}$ substituted or unsubstituted 5- or 6-membered aliphatic or aromatic hydrocarbon rings, each of which are optionally substituted with halogen.

In some embodiments, R1 and R2 and/or R7 and R8 in formula (I) form a 5- or 6-membered aliphatic or aromatic hydrocarbon ring optionally substituted with halogen; and R3 is linear or branched unsaturated or saturated $C_1$-$C_{12}$ alkyl or R3 is linear or branched $C_1$-$C_{12}$, alkoxy.

In some embodiments, X in formula (I) is O.

According to some embodiments, the internal electron donor compound of formula (I) is (D-1) which is shown below

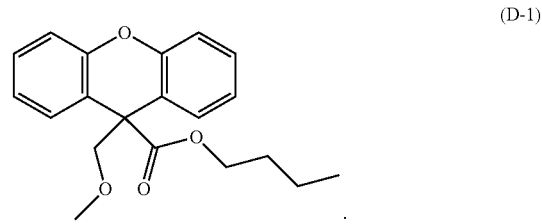 [SMILES: CCCCOC(=O)C1(COC)c2ccccc2Oc2ccccc21]

(D-1)

According to another embodiment, a catalyst system for polymerization of an olefin is provided. This catalyst system comprises: the olefin polymerization catalyst component of formula (I) discussed hereinabove; a titanium compound and/or a magnesium compound; an organoaluminum compound; and c) optionally an external electron donor.

In some embodiments, the magnesium compound can be magnesium halide, in particular, magnesium chloride and the titanium compound can be titanium halide, in particular, $TiCl_4$ or $TiCl_3$.

In other embodiments, the titanium compound can be a tetravalent titanium compound represented by chemical formula (A):

$$Ti(OR)_gX_{4-g} \quad (A)$$

wherein R represents a hydrocarbon group, preferably an alkyl group having 1 to about 20 carbon atoms, X represents a halogen atom, and $0 \leq g \leq 4$. Specific examples of the titanium compound include, but are not limited to titanium tetrahalides such as $TiCl_4$, $TiBr_4$ and $TiI_4$; alkoxytitanium trihalides such as $Ti(OCH_3)Cl_3$, $Ti(OC_2H_5)Cl_3$, $Ti(O-n-C_4H_9)Cl_3$, $Ti(OC_2H_5)Br_3$ and $Ti(O-i-C_4H_9)Br_3$; dialkoxytitanium dihalides such as $Ti(OCH_3)_2Cl_2$, $Ti(OC_2H_5)_2Cl_2$, $Ti(O-n-C_4H_9)_2Cl_2$ and $Ti(OC_2H_5)_2Br_2$; trialkoxytitanium monohalides such as $Ti(OCH_3)_3Cl$, $Ti(OC_2H_5)_3Cl$, $Ti(O-n-C_4H_9)_3Cl$ and $Ti(OC_2H_5)_3Br$; and tetraalkoxytitaniums such as $Ti(OCH_3)_4$, $Ti(OC_2H_5)_4$ and $Ti(O-n-C_4H_9)_4$. Among these, the halogen containing titanium compounds, especially titanium tetrahalides, are preferred in some instances. These titanium compounds may be used individually or in solutions of hydrocarbon compounds or halogenated hydrocarbons.

The magnesium compounds include, for example, a magnesium compound having no reducibility. In one embodiment, the magnesium compound having no reducibility is a halogen containing magnesium compound. Specific examples of the magnesium compound having no reducibility include, but are not limited to magnesium halides such as magnesium chloride, magnesium bromide, magnesium iodide and magnesium fluoride; alkoxy magnesium halides such as methoxy magnesium chloride, ethoxy magnesium chloride, isopropoxy magnesium chloride, butoxy magnesium chloride and octoxy magnesium chloride; aryloxy magnesium halides such as phenoxy magnesium chloride and methylphenoxy magnesium chloride; alkoxy magnesiums such as ethoxy magnesium, isopropoxy magnesium, butoxy magnesium, n-octoxy magnesium and 2-ethylhexoxy magnesium; aryloxy magnesiums such as phenoxy magnesium and dimethylphenoxy magnesium; and carboxylic acid salts of magnesium such as magnesium laurate and magnesium stearate. These magnesium compounds may be in the liquid or solid state.

When preparing the olefin polymerization catalyst component, the internal electron donor of formula (I) can be used/added. The solid titanium catalyst component can be made by contacting a magnesium compound and a titanium compound with the internal electron donor compound. In one embodiment, the titanium catalyst component is made by contacting a magnesium compound and a titanium compound in the presence of an internal electron donor compound. In another embodiment, the titanium catalyst component is made by forming a magnesium based catalyst support optionally with the titanium compound and optionally with the internal electron donor compound, and contacting the magnesium based catalyst support with the titanium compound and the internal electron donor compound.

In some embodiments, the organoaluminum compound of the catalyst system discussed hereinabove, is an alkyl-aluminum compound. The alkyl-aluminum compound can be a trialkyl aluminum compound. The trialkyl aluminum compound, in some embodiments, can be selected from the group consisting of triethylaluminum, triisobutylaluminum, and tri-n-octylaluminum, and combinations thereof.

The catalyst system can further comprise esters, phthalate compounds, ketones, and/or ethers.

According to one embodiment, a process for polymerizing or copolymerizing an olefin is provided. The process comprises: (a) providing the catalyst system discussed hereinabove; (b) polymerizing or copolymerizing the olefin in a presence of the catalyst system to form a polymer or a copolymer; and (c) optionally recovering the polymer or the copolymer.

The olefin can be selected from the group consisting of ethylene, propylene, 1-butylene, 4-methyl-1-pentente, 1-hexene, 1-octene, and mixtures thereof.

According to another embodiment, a catalyst system for polymerization of an olefin comprising a catalyst component comprising an internal electron donor compound shown in formula (I) below is provided:

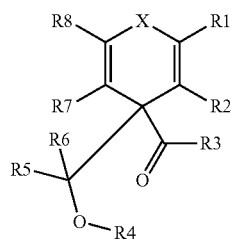

(I)

wherein
X is O, S, $NR^a$, $PR^b$, or $POOR^c$,
wherein $R^a$ is independently hydrogen or halogen, or wherein $R^a$ is independently carbonyl hydrocarbon, linear or branched unsaturated or saturated alkyl hydrocarbon, cyclic, aromatic, or aliphatic hydrocarbon, each of which are optionally substituted with halogen,
wherein $R^b$ is independently hydrogen or halogen, or wherein $R^b$ is independently carbonyl hydrocarbon, linear or branched unsaturated or saturated alkyl hydrocarbon, linear or branched unsaturated or saturated alkoxy hydrocarbon, cyclic, aromatic, or aliphatic hydrocarbon, each of which are optionally substituted with halogen, wherein $R^c$ is hydrogen, or wherein $R^c$ is carbonyl hydrocarbon, linear or branched unsaturated or saturated alkyl hydrocarbon, cyclic, aromatic, or aliphatic hydrocarbon, each of which are optionally substituted with halogen,
R1-R8 are identical or different hydrogen or halogen, or
R1-R8 are identical or different linear or branched unsaturated or saturated $C_1$-$C_{30}$ alkyl, alone or in combination with $C_5$-$C_{30}$ substituted or unsubstituted 5- or 6-membered aliphatic or aromatic hydrocarbon rings, each of which are optionally substituted with halogen.

In some embodiments, X in formula (I) is O; R1 and R2 and/or R7 and R8 in formula (I) form a 5- or 6-membered hydrocarbon ring optionally substituted with halogen; and R3 in formula (I) is linear or branched unsaturated or saturated $C_1$-$C_{12}$ alkyl or R3 is linear or branched $C_1$-$C_{12}$ alkoxy.

In some embodiments, a catalyst system for use in olefinic polymerization is provided. The catalyst system comprises: the olefin polymerization catalyst component of formula (I) discussed hereinabove; an organoaluminum compound; and an organosilicon compound.

In some embodiments, the organoaluminum compound is an alkyl-aluminum compound. The alkyl-aluminum compound can be a trialkyl aluminum compound. The trialkyl aluminum compound can be selected from the group consisting of triethylaluminum, triisobutylaluminum, and tri-n-octylaluminum, and combinations thereof.

The organosilicon compound in some embodiments can be represented by chemical formula (II) shown below:

$$R_nSi(OR')_{4-n} \quad (II)$$

wherein each R and R' independently represent a hydrocarbon group, and n is $0 \leq n \leq 4$.

In other embodiments, the organosilicon compound is represented by chemical formula (III) shown below:

$$SiRR'_m(OR'')_{3-m} \quad (III)$$

wherein R independently represents a cyclic hydrocarbon or substituted cyclic hydrocarbon group, wherein each R' and R" independently represent a hydrocarbon group, and wherein m is an integer from 0 to 2.

According to some embodiments, a process of polymerizing or copolymerizing an olefin monomer is provided. The process comprises: (i) providing the catalyst system discussed hereinabove; (ii) polymerizing or copolymerizing the olefin monomer in the presence of the catalyst system to form a polymer or a copolymer; and (iii) optionally recovering the polymer or the copolymer.

The olefin monomer can be selected from the group consisting of ethylene, propylene, 1-butylene, 4-methyl-1-pentene, 1-hexane, 1-octene, and combinations thereof.

The internal electron donor compounds may be used individually or in combination. In employing the internal electron donor compounds, they do not have to be used directly as starting materials, but compounds convertible to the electron donors in the course of preparing the solid catalyst components may also be used as the starting materials.

In one embodiment, the olefin polymerization catalyst component is made by contacting a magnesium compound and a titanium compound in the presence of the internal electron donor compound of formula (I) discussed hereinabove. In another embodiment, the olefin polymerization catalyst component is made by forming a magnesium based catalyst support/catalyst crystal lattice optionally with a titanium compound and with the internal electron donor compound of formula (I) discussed hereinabove, and contacting the magnesium based catalyst support/catalyst crystal lattice with the titanium compound and the internal electron donor compound. In yet another embodiment, the olefin polymerization catalyst component is made by contacting a magnesium based catalyst support/catalyst crystal lattice with a titanium compound to form a mixture, then contacting the mixture with the internal electron donor compound of formula (I) discussed hereinabove. In still yet another embodiment, the olefin polymerization catalyst component is made by contacting a magnesium based catalyst support/catalyst crystal lattice with a titanium compound to form a mixture, then contacting the mixture with the internal electron compound of formula (I) discussed hereinabove, then contacting the mixture again with the internal electron donor compound of formula (I) discussed hereinabove. Such repeated contact with the internal electron donor compound of formula (I) discussed hereinabove can occur once, twice, three times, four times or more, successively or with other acts performed between contacts with additional doses of the internal electron donor compound of formula (I) discussed hereinabove.

Generally speaking, the magnesium based catalyst support/catalyst crystal lattice is made by dissolving a magnesium compound in a solvent mixture comprising an organic epoxy compound, an organic phosphorus compound and an optional inert diluent to form a homogenous solution.

The organic epoxy compounds used herein include compounds having at least one epoxy group in the forms of monomers, dimers, oligomers and polymers. Examples of epoxy compounds include, but are not limited to aliphatic epoxy compounds, alicyclic epoxy compounds, aromatic epoxy compounds, or the like. Examples of aliphatic epoxy compounds include, but are not limited to halogenated aliphatic epoxy compounds, aliphatic epoxy compounds having a keto group, aliphatic epoxy compounds having an ether bond, aliphatic epoxy compounds having an ester bond, aliphatic epoxy compounds having a tertiary amino group, aliphatic epoxy compounds having a cyano group, or the like. Examples of alicyclic epoxy compounds include, but are not limited to halogenated alicyclic epoxy compounds, alicyclic epoxy compounds having a keto group, alicyclic epoxy compounds having an ether bond, alicyclic epoxy compounds having an ester bond, alicyclic epoxy compounds having a tertiary amino group, alicyclic epoxy compounds having a cyano group, or the like. Examples of aromatic epoxy compounds include, but are not limited to halogenated aromatic epoxy compounds, aromatic epoxy compounds having a keto group, aromatic epoxy compounds having an ether bond, aromatic epoxy compounds having an ester bond, aromatic epoxy compounds having a tertiary amino group, aromatic epoxy compounds having a cyano group, or the like.

Specific examples of epoxy compounds include, but are not limited to epifluorohydrin, epichlorohydrin, epibromohydrin, hexafluoropropylene oxide, 1,2-epoxy-4-fluorobutane, 1-(2,3-epoxypropyl)-4-fluorobenzene, 1-(3,4-epoxybutyl)-2-fluorobenzene, epoxypropyl)-4-chlorobenzene, 1-(3,4-epoxybutyl)-3-chlorobenzene, or the like. Specific examples of halogenated alicyclic epoxy compounds include 4-fluoro-1,2-cyclohexene oxide, 6-chloro-2,3 epoxybicyclo[2,2,1]heptane, or the like. Specific examples of halogenated aromatic epoxy compounds include 4-fluorostyrene oxide, 1-(1,2-epoxypropyl)-3-trifluorobenzene, or the like.

The organic phosphorus compounds used herein include, but are not limited to hydrocarbyl esters and halohydrocarbyl esters of ortho-phosphoric acid and phosphorous acid. Specific examples include, but are not limited to trimethyl phosphate, triethyl phosphate, tributyl phosphate, triphenyl phosphate, trimethyl phosphite, triethyl phosphite, tributyl phosphite and triphenyl phosphite.

For more sufficiently dissolving a magnesium compound, an inert diluent is optionally added in the solvent mixture. The inert diluent can typically be aromatic hydrocarbons or alkanes, as long as it can facilitate the dissolution of the magnesium compound. Examples of aromatic hydrocarbons include, but are not limited to benzene, toluene, xylene, chlorobenzene, dichlorobenzene, trichlorobenzene, chlorotoluene, and derivatives thereof. Examples of alkanes include linear, branched, or cyclic alkanes having about 3 to about 30 carbons, such as butane, pentane, hexane, cyclohexane, heptanes, and the like. These inert diluents may be used alone or in combination.

In embodiments of making the olefin polymerization catalyst component, the magnesium based catalyst support/catalyst crystal lattice is mixed with a titanium compound such as liquid titanium tetrahalide to form a solid precipitate in the optional presence of an auxiliary precipitant. The auxiliary precipitant may be added before, during or after the precipitation of the solids and loaded on the solids.

The auxiliary precipitants used herein include carboxylic acids, carboxylic acid anhydrides, ethers, ketones, or mixture thereof. Specific examples include, but are not limited to acetic anhydride, phthalic anhydride, succinic anhydride, maleic anhydride, 1,2,4,5-benzene tetracarboxylic dianhydride, acetic acid, propionic acid, butyric acid, acrylic acid, methacrylic acid, acetone, methyl ethyl ketone, benzophenone, dimethyl ether, diethyl ether, dipropyl ether, dibutyl ether, and dipentyl ether.

The process of solids precipitation can be carried out by at least one of three methods. One method involves mixing a titanium compound such as liquid titanium tetrahalide with a magnesium based catalyst support/catalyst crystal lattice at a temperature in the range of about −40° C. to about 0° C., and precipitating the solids while the temperature is raised slowly to a range from about 30° C. to about 120° C., such as from about 60° C. to about 100° C. The second method involves adding a titanium compound dropwise into a magnesium based catalyst support/catalyst crystal lattice at low or room temperature to precipitate out solids immediately. The third method involves adding a first titanium compound dropwise into a magnesium based catalyst support/catalyst crystal lattice and mixing a second titanium compound with the magnesium catalyst support/catalyst crystal lattice. In these methods, an internal electron donor compound can be desirably present in the reaction system. The internal electron donor compound of formula (I) discussed hereinabove can be added either after the magnesium based catalyst support/catalyst crystal lattice is obtained or after the solid precipitate is formed.

In one embodiment, when the olefin polymerization catalyst component is formed, a surfactant can be used. The surfactant can contribute to many of the beneficial properties of the olefin polymerization catalyst component and catalyst system. General examples of surfactants include polymer surfactants, such as polyacrylates, polymethacrylates, polyalkyl methacrylates, and the like. A polyalkyl methacrylate is a polymer that may contain one or more methacrylate monomers, such as at least two different methacrylate monomers, at least three different methacrylate monomers, etc. Moreover, the acrylate and methacrylate polymers may contain monomers other than acrylate and methacrylate monomers, so long as the polymer surfactant contains at least about 40% by weight acrylate and methacrylate monomers.

In one embodiment, non-ionic surfactants and/or anionic surfactants can be used. Examples of non-ionic surfactants and/or anionic surfactants include, but are not limited to phosphate esters, alkyl sulfonates, aryl sulfonates, alkylaryl sulfonates, linear alkyl benzene sulfonates, alkylphenols, ethoxylated alcohols, carboxylic esters, fatty alcohols, fatty esters, fatty aldehydes, fatty ketones, fatty acid nitrites, benzene, naphthalene, anthracene, succinic anhydride, phthalic anhydrides, rosin, terpene, phenol, or the like. In fact, a number of anhydride surfactants are effective. In some instances, the absence of an anhydride surfactant causes the formation of very small catalyst support particles while the over-use creates straw shaped material sometimes referred to as needles.

The olefin polymerization catalyst precursor can be formed in the following way. In a solvent such as toluene, a magnesium and titanium containing solution is seen following the addition of a halogenating agent such as $TiCl_4$ into a magnesium based solution at relatively cooler temperatures, such as −25° C. until about 0° C. An oil phase is then formed, which can be dispersed into the hydrocarbon phase that is stable until about 40° C. The resultant magnesium material becomes a semi-solid at this point and the particle morphology is now determined. The semi-solid converts to a solid between about 40° C. and about 80° C.

To facilitate obtaining uniform solid particles, the process of precipitation can be carried out slowly. When the second method of adding titanium halide dropwise at low or room temperature is applied, the process may take place over a period from about 1 hour to about 6 hours. When the first method of raising the temperature in a slow manner is applied, the rate of temperature increase can range from about 4° C. to about 125° C. per hour.

The solid precipitate is first separated from the mixture. In the solid precipitate thus obtained may be entrained a variety of complexes and byproducts, so that further treatment may in some instances be necessary. In one embodiment, the solid precipitate is treated with a titanium compound to substantially remove the byproducts from the solid precipitate.

The solid precipitate can be washed with an inert diluent and then treated with a titanium compound or a mixture of a titanium compound and an inert diluent. The titanium compound used in this treatment can be identical to or different with the titanium compound used for forming the solid precipitate. The amount of titanium compound used is from about 1 to about 20 moles, such as from about 2 to about 15 moles, per mole of magnesium compound in the support. The treatment temperature ranges from about 50° C. to about 150° C., such as from about 60° C. to about 100° C. If a mixture of titanium tetrahalide and an inert diluent is used to treat the solid precipitate, the volume % of titanium tetrahalide in the treating solution is from about 10% to about 100%, the rest being the inert diluent.

The treated solids can be further washed with an inert diluent to remove ineffective titanium compounds and other byproducts. The inert diluent herein used can be hexane, heptanes, octane, 1,2-dichloroethane, benzene, toluene, ethylbenzene, xylene, and other hydrocarbons.

By treating the solid precipitate with the titanium compound and optionally an inert diluent, the byproducts in the solid precipitate can be removed from the solid precipitate. In one embodiment, the solid precipitate is treated with the titanium compound and optionally an inert diluent about two times or more and five times or less.

By treating the solid precipitate with an inert diluent, a free titanium compound in the solid precipitate can be removed from the solid precipitate. As a result, the resultant solid precipitate does not substantially contain a free titanium compound. In one embodiment, the solid precipitate is treated repeatedly with an inert diluent until the filtrate contains about 100 ppm or less of titanium. In another embodiment, the solid precipitate is treated repeatedly with an inert diluent until the filtrate contains about 50 ppm or less of titanium. In yet another embodiment, the solid precipitate is treated with an inert diluent until the filtrate contains about 10 ppm or less of titanium. In one embodiment, the solid precipitate is treated with an inert diluent about three times or more and seven times or less.

In one embodiment, the olefin polymerization catalyst component contains from about 0.5 to about 6.0 wt % titanium; from about 10 to about 25 wt % magnesium; from about 40 to about 70 wt % halogen; from about 1 to about 50 wt % the internal electron donor compound of formula (I) discussed hereinabove; and optionally inert diluent from about 0 to about 15 wt %. In another embodiment, the olefin polymerization catalyst component contains from about 2 to about 25 wt % of one or more of the internal electron donor compound of formula (I) discussed hereinabove. In yet another embodiment, the olefin polymerization catalyst component contains from about 5 to about 20 wt % of one or more of the internal electron donor compound of formula (I) discussed hereinabove.

The amounts of the ingredients used in preparing the olefin polymerization catalyst component may vary depending upon the method of preparation. In one embodiment, from about 0.01 to about 5 moles of the internal electron donor compound of formula (I) discussed hereinabove and from about 0.01 to about 500 moles of the titanium compounds are used per mole of the magnesium compound used to make the olefin polymerization catalyst component. In another embodiment, from about 0.05 to about 2 moles of the internal electron donor compound of formula (I) discussed hereinabove and from about 0.05 to about 300 moles of the titanium compounds are used per mole of the magnesium compound used to make the olefin polymerization catalyst component.

In one embodiment, in the olefin polymerization catalyst component, the atomic ratio of halogen/titanium is from about 4 to about 200; the internal electron donor/titanium mole ratio is from about 0.01 to about 10; and the magnesium/titanium atomic ratio is from about 1 to about 100. In another embodiment, in the olefin polymerization catalyst component, the atomic ratio of halogen/titanium is from about 5 to about 100; the internal electron donor/titanium mole ratio is from about 0.2 to about 6; and the magnesium/titanium atomic ratio is from about 2 to about 50.

The resulting olefin polymerization catalyst component generally contains a magnesium halide of a smaller crystal size than commercial magnesium halides and usually has a specific surface area of at least about 5 $m^2/g$, such as from about 10 to about 1,000 $m^2/g$, or from about 100 to about 800 $m^2/g$. As the above ingredients are unified to form an integral structure of the olefin polymerization catalyst component, the composition of the olefin polymerization catalyst component does not substantially change by washing with, for example, hexane.

The olefin polymerization catalyst component may be used after being diluted with an inorganic or organic compound such as a silicon compound, an aluminum compound, or the like.

Methods of preparing olefin polymerization catalyst components, which can be used herein, are described in U.S. Pat. Nos. 4,771,023; 4,784,983; 4,829,038; 4,861,847; 4,990,479; 5,177,043; 5,194,531; 5,244,989; 5,438,110; 5,489,634; 5,576,259; 5,767,215; 5,773,537; 5,905,050; 6,323,152; 6,437,061; 6,469,112; 6,962,889; 7,135,531; 7,153,803; 7,271,119; U.S. Patent Publication Nos: 2004242406; 20040242407; and 20070021573 which are hereby incorporated by reference in this regard.

The catalyst system may contain at least one organoaluminum compound in addition to the olefin polymerization catalyst component. Compounds having at least one aluminum-carbon bond in the molecule can be used as the organoaluminum compound. Examples of organoaluminum compounds include compounds of the following chemical formula (B):

$$AlR_nX_{3-n} \quad (B)$$

In formula (B), R independently represents a hydrocarbon group usually having 1 to about 20 carbon atoms, X represents a halogen atoms, and $0<n\leq3$.

Specific examples of the organoaluminum compounds represented by formula (B) include, but are not limited to trialkyl aluminums such as triethyl aluminum, tributyl aluminum and trihexyl aluminum; trialkenyl aluminums such as triisoprenyl aluminum; dialkyl aluminum halides such as diethyl aluminum chloride, dibutyl aluminum chloride and diethyl aluminum bromide; alkyl aluminum sesquihalides such as ethyl aluminum sesquichloride, butyl aluminum sesquichloride and ethyl aluminum sesquibromide; alkyl aluminum dihalides such as ethyl aluminum dichloride, propyl aluminum dichloride and butyl aluminum dibromide; dialkyl aluminum hydrides such as diethyl aluminum hydride and dibutyl aluminum hydride; and other partially hydrogenated alkyl aluminum such as ethyl aluminum dihydride and propyl aluminum dihydride.

The organoaluminum compound is used in the catalyst system in an amount that the mole ratio of aluminum to titanium (from the olefin polymerization catalyst component) is from about 5 to about 1,000. In another embodiment, the mole ratio of aluminum to titanium in the catalyst system is from about 10 to about 700. In yet another embodiment, the mole ratio of aluminum to titanium in the catalyst system is from about 25 to about 400.

The catalyst system may contain at least one organosilicon compound in addition to the olefin polymerization catalyst component. This organosilicon compound is sometimes termed as an external electron donor. The organosilicon compound contains silicon having at least one hydrogen ligand (hydrocarbon group). General examples of hydrocarbon groups include alkyl groups, cycloalkyl groups, (cycloalkyl)methylene groups, alkene groups, aromatic groups, and the like.

The organosilicon compound, when used as an external electron donor serving as one component of a Ziegler-Natta catalyst system for olefin polymerization, contributes to the ability to obtain a polymer (at least a portion of which is polyolefin) having a controllable molecular weight distribution and controllable crystallinity while retaining high performance with respect to catalytic activity.

The organosilicon compound is used in the catalyst system in an amount that the mole ratio of the organoaluminum compound to the organosilicon compound is from about 2 to about 90. In another embodiment, the mole ratio of the organoaluminum compound to the organosilicon compound is from about 5 to about 70. In yet another embodiment, the mole ration of the organoaluminum compound to the organosilicon compound is from about 7 to about 35.

In one embodiment, as discussed hereinabove, the organosilicon compound is represented by chemical formula (II):

$$R_nSi(OR')_{4-n} \quad (II)$$

wherein each R and R' independently represent a hydrocarbon group, and n is $0\leq n\leq4$.

Specific examples of the organosilicon compound of formula (II) include, but are not limited to trimethylmethoxysilane, trimethylethoxysilane, dimethyldimethoxysilane, dimethyldiethoxysilane, diisopropyldimethoxysilane, diisobutyldimethoxysilane, t-butylmethyldimethoxysilane, t-butylmethyldiethoxysilane, t-amylmethyldiethoxysilane, dicyclopentyldimethoxysilane, diphenyldimethoxysilane, phenylmethyldimethoxysilane, diphenyldiethoxysilane, bis-o-tolydimethoxysilane, bis-m-tolydimethoxysilane, bis-p-tolydimethoxysilane, bis-p-tolydiethoxysilane, bisethylphenyldimethoxysilane, dicyclohexyldimethoxysilane, cyclohexylmethyldimethoxysilane, cyclohexylmethyldiethoxysilane, ethyltrimethoxysilane, ethyltriethoxysilane, vinyltrimethoxysilane, methyltrimethoxysilane, n-propyltriethoxysilane, decyltrimethoxysilane, decyltriethoxysilane, phenyltrimethoxysilane, gamma-chloropropyltrimethoxysilane, methyltriethoxysilane, ethyltriethoxysilane, vinyltriethoxysilane, t-butyltriethoxysilane, n-butyltriethoxysilane, iso-butyltriethoxysilane, phenyltriethoxysilane, gamma-aminopropyltriethoxysilane, cholotriethoxysilane, ethyltriisopropoxysilane, vinyltirbutoxysilane, cyclohexyltrimethoxysilane, cyclohexyltriethoxysilane, 2-norbornanetrimethoxysilane, 2-norbornanetriethoxysilane, 2-norbornanemethyldimethoxysilane, ethyl silicate, butyl silicate, trimethylphenoxysilane, and methyltriallyloxysilane.

In another embodiment, as described hereinabove, the organosilicon compound is represented by chemical formula (III):

$$SiRR'_m(OR'')_{3-m} \quad (III)$$

wherein R, R', R", and m are defined hereinabove.

Specific examples of the group R include, but are not limited to cyclopropyl; cyclobutyl; cyclopentyl; 2-methylcyclopentyl; 3-methylcyclopentyl; 2-ethylcyclopentyl; 3-propylcyclopentyl; 3-isopropylcyclopentyl; 3-butylcyclopentyl; 3-tertiary butyl cyclopentyl; 2,2-dimethylcyclopentyl; 2,3-dimethylcyclopentyl; 2,5-dimethylcyclopentyl; 2,2,5-trimethylcyclopentyl; 2,3,4,5-tetramethylcyclopentyl; 2,2,5,5-tetramethylcyclopentyl; 1-cyclopentylpropyl; 1-methyl-1-cyclopentylethyl; cyclopentenyl; 2-cyclopentenyl; 3-cyclopentenyl; 2-methyl-1-cyclopentenyl; 2-methyl-3-cyclopentenyl; 3-methyl-3-cyclopentenyl; 2-ethyl-3-cyclopentenyl; 2,2-dimethyl-3-cyclopentenyl; 2,5-dimethyl-3-cyclopentenyl; 2,3,4,5-tetramethyl-3-cyclopentenyl; 2,2,5,5-tetramethyl-3-cyclopentenyl; 1,3-cyclopentadienyl; 2,4-cyclopentadienyl; 1,4-cyclopentadienyl; 2-methyl-1,3-cyclopentadienyl; 2-methyl-2,4-cyclopentadienyl; 3-methyl-2,4-cyclopentadienyl; 2-ethyl-2,4-cyclopentadienyl; 2,2-dimethyl-2,4-cyclopentadienyl; 2,3-dimethyl-2,4-cyclopentadienyl; 2,5-dimethyl-2,4-cyclopentadienyl; 2,3,4,5-tetramethyl-2,4-cyclopentadienyl; indenyl; 2-methylindenyl; 2-ethylindenyl; 2-indenyl; 1-methyl-2-indenyl; 1,3-dimethyl-2-indenyl; indanyl; 2-methylindanyl; 2-indanyl; 1,3-dimethyl-2-indanyl; 4,5,6,7-tetrahydroindenyl; 4,5,6,7-tetrahydro-2-indenyl; 4,5,6,7-tetrahydro-1-methyl-2-indenyl; 4,5,6,7-tetrahydro-1,3-dimethyl-2-indenyl; fluorenyl groups; cyclohexyl; methylcyclohexyls; ethylcylcohexyls; propylcyclohexyls; isopropylcyclohexyls; n-butylcyclohexyls; tertiary-butyl cyclohexyls; dimethylcyclohexyls; and trimethylcyclohexyls.

R' and R" are identical or different and each represents a hydrocarbons. Examples of R' and R" are alkyl, cycloalkyl, aryl and aralkyl groups having 3 or more carbon atoms. Furthermore, R and R' may be bridged by an alkyl group, etc. General examples of organosilicon compounds are those of formula (III) in which R is cyclopentyl group, R' is an alkyl group such as methyl or cyclopentyl group, and R" is an alkyl group, particularly a methyl or ethyl group.

Specific examples of organosilicon compound of formula (III) include, but are not limited to trialkoxysilanes such as cyclopropyltrimethoxysilane, cyclobutyltrimethoxysilane, cyclopentyltrimethoxysilane, 2-methylcyclopentyltrimethoxysilane, 2,3-dimethylcyclopentyltrimethoxysilane, 2,5-dimethylcyclopentyltrimethoxysilane, cyclopentyltriethoxysilane, cyclopentenyltrimethoxysilane, 3-cyclopentenyltrimethoxysilane, 2,4-cyclopentadienyltrimethoxysilane, indenyltrimethoxysilane and fluorenyltrimethoxysilane; dialkoxysilanes such as dicyclopentyldimethoxysilane, bis(2-methylcyclopentyl)dimethoxysilane, bis(3-tertiary butyl-cyclopentyl)dimethoxysilane, bis(2,3-dimethylcyclopentyl) dimethoxysilane, bis(2,5-dimethylcyclopentyl) dimethoxysilane, dicyclopentyldiethoxysilane, dicyclobutyldiethoxysilane, cyclopropylcyclobutyldiethoxysilane, dicyclopentenyldimethoxysilane, di(3-cyclopentenyl)dimethoxysilane, bis(2,5-dimethyl-3-cyclopentenyl)dimethoxysilane, di-2,4-cyclopentadienyl)dimethoxysilane, bis(2,5-dimethyl-2,4-cyclopentadienyl)dimethoxysilane, bis(1-methyl-1-cyclopentylethyl)dimethoxysilane, cyclopentylcyclopentenyldimethoxysilane, cyclopentylcyclopentadienyldimethoxysilane, diindenyldimethoxysilane, bis(1,3-dimethyl-2-indenyl)dimethoxysilane, cyclopentadienylindenyldimethoxysilane, difluorenyldimethoxysilane, cyclopentylfluorenyldimethoxysilane and indenylfluorenyldimethoxysilane; monoalkoxysilanes such as tricyclopentylmethoxysilane, tricyclopentenylmethoxysilane, tricyclopentadienylmethoxysilane, tricyclopentylethoxysilane, dicyclopentylmethylmethoxysilane, dicyclopentylethylmethoxysilane, dicyclopentylmethylethoxysilane, cyclopentyldimethylmethoxysilane, cyclopentyldiethylmethoxysilane, cyclopentyldimethylethoxysilane, bis(2,5-dimethylcyclopentyl)cyclopentylmethoxysilane, dicyclopentylcyclopentenylmethoxysilane, dicyclopentylcyclopentenadienylmethoxysilane and diindenylcyclopentylmethoxysilane; and ethylenebis-cyclopentyldimethoxysilane.

Polymerization of olefins in this application is carried out in the presence of the catalyst system described above. Generally speaking, olefins are contacted with the catalyst system described above under suitable conditions to form desired polymer products. In one embodiment, preliminary polymerization described below is carried out before the main polymerization. In another embodiment, polymerization is carried out without preliminary polymerization. In yet another embodiment, the formation of copolymer is carried out using at least two polymerization zones.

In preliminary polymerization, the olefin polymerization catalyst component is usually employed in combination with at least a portion of the organoaluminum compound. This may be carried out in the presence of part or the whole of the organosilicon compound (external electron donor compound). The concentration of the catalyst system used in the preliminary polymerization may be much higher than that in the reaction system of the main polymerization.

In preliminary polymerization, the concentration of the olefin polymerization catalyst component in the preliminary polymerization is usually from about 0.01 to about 200 millimoles, preferably from about 0.05 to about 100 millimoles, calculated as titanium atoms per liter of an inert hydrocarbon medium described below. In one embodiment, the preliminary polymerization is carried out by adding an olefin and the above catalyst system ingredients to an inert hydrocarbon medium and polymerizing the olefin under mild conditions.

Specific examples of the inert hydrocarbon medium include, but are not limited to aliphatic hydrocarbons such as propane, butane, pentane, hexane, heptanes, octane, decane, dodecane and kerosene; alicyclic hydrocarbons such as cyclopentane, cyclohexane and methylcyclopentane; aromatic hydrocarbons such as benzene, toluene and xylene; and mixtures thereof. In the present application, a liquid olefin may be used in place of part or the whole of the inert hydrocarbon medium.

The olefin used in the preliminary polymerization may be the same as, or different from, an olefin to be used in the main polymerization.

The reaction temperature for the preliminary polymerization is sufficient for the resulting preliminary polymer to not substantially dissolve in the inert hydrocarbon medium. In one embodiment, the temperature is from about −20° C. to about 100° C. In another embodiment, the temperature is from about −10° C. to about 80° C. In yet another embodiment, the temperature is from about 0° C. to about 40° C.

Optionally, a molecular-weight controlling agent, such as hydrogen, may be used in the preliminary polymerization. The molecular weight controlling agent is used in such an amount that the polymer obtained by the preliminary polymerization has an intrinsic viscosity, measured in decalin at 135° C., of at least about 0.2 dl/g, and preferably from about 0.5 to 10 dl/g.

In one embodiment, the preliminary polymerization is desirably carried out so that from about 0.1 g to about 1,000 g of a polymer is formed per gram of the olefin polymerization catalyst component of the catalyst system. In another embodiment, the preliminary polymerization is desirably carried out so that from about 0.3 g to about 500 g of a polymer is formed per gram of the olefin polymerization catalyst component. If the amount of the polymer formed by the preliminary polymerization is too large, the efficiency of producing the olefin polymer in the main polymerization may sometimes decrease, and when the resulting olefin polymer is molded into a film or another article, fish eyes tend to occur in the molded article. The preliminary polymerization may be carried out batchwise or continuously.

After the preliminary polymerization conducted as above, or without performing any preliminary polymerization, the main polymerization of an olefin is carried out in the presence of the above-described olefin polymerization catalyst system formed from the olefin polymerization catalyst component, the organoaluminum compound and the organosilicon compound (external electron donor compound).

Examples of olefins that can be used in the main polymerization are alpha-olefins having 2 to 20 carbon atoms such as ethylene, propylene, 1-butene, 4-methyl-1-pentene, 1-pentene, 1-octene, 1-hexene, 3-methyl-1-pentene, 3-methyl-1-butene, 1-decene, 1-tetradecene, 1-eicosene, and vinylcyclohexane. In the process of the present application, these alpha-olefins may be used individually or in any combination.

In one embodiment, propylene or 1-butene is homopolymerized, or a mixed olefin containing propylene or 1-butene as a main component is copolymerized. When the mixed olefin is used, the proportion of propylene or 1-butene as the main component is usually at least about 50 mole %, preferably at least about 70 mole %.

By performing the preliminary polymerization, the catalyst system in the main polymerization can be adjusted in the degree of activity. This adjustment tends to result in a powdery polymer having a high bulk density. Furthermore, when the preliminary polymerization is carried out, the particles shape of the resulting polymer becomes spherical, and in the case of slurry polymerization, the slurry attains excellent characteristics while in the case of gas phase polymerization, the polymer seed bed attains excellent characteristics. Furthermore, in these embodiments, a polymer having a high stereoregularity index can be produced with a high catalytic efficiency by polymerizing an alpha-olefin having at least 3 carbon atoms. Accordingly, when producing the propylene copolymer, the resulting copolymer powder or the copolymer becomes easy to handle.

In the homopolymerization of these olefins, a polyunsaturated compound such as conjugated diene or non-conjugated diene may be used as a comonomer. Examples of comonomers include styrene, butadiene, acrylonitrile, acrylamide, alpha-methyl styrene, chlorostyrene, vinyl toluene, divinyl benzene, diallylphthalate, alkyl methacrylates and alkyl acrylates. In one embodiment, the comonomers include thermoplastic and elastomeric monomers.

The main polymerization of an olefin is carried out usually in the gaseous or liquid phase. In one embodiment, polymerization (main polymerization) employs a catalyst system containing the olefin polymerization catalyst component in an amount from about 0.001 to about 0.75 millimoles calculated as Ti atom per liter of the volume of the polymerization zone, the organoaluminum compound in an amount from about 1 to about 2,000 moles per mole of titanium atoms in the olefin polymerization catalyst component, and the organosilicon compound in an amount from about 0.001 to about 10 moles calculated as Si atoms in the organosilicon compound per mole of the metal atoms in the organoaluminum compound. In another embodiment, polymerization employs a catalyst system containing the olefin polymerization catalyst component in an amount of from 0.005 to about 0.5 millimoles calculated as Ti atom per liter of the volume of the polymerization zone, the organoaluminum compound in an amount from about 5 to about 500 moles per mole of titanium atoms in the olefin polymerization catalyst component, and the organosilicon compound in an amount from about 0.01 to about 2 moles calculated as Si atoms in the organosilicon compound per mole of the metal atoms in the organoaluminum compound. In yet another embodiment, polymerization employs a catalyst system containing the alkyl benzoate derivative in an amount from about 0.005 to about 1 mole calculated as Si atoms in the organosilicon compound per mole of the metal atoms in the organoaluminum compound.

When the organoaluminum compound and the organosilicon compound are used partially in the preliminary polymerization, the catalyst system subjected to the preliminary polymerization is used together with the remainder of the catalyst system components. The catalyst system subjected to the preliminary polymerization may contain the preliminary polymerization product.

The use of hydrogen at the time of polymerization promotes and contributes to control of the molecular weight of the resulting polymer, and the polymer obtained may have a high melt flow rate. In this case, the stereoregularity index of the resulting polymer and the activity of the catalyst system are increased according to the methods of the present application.

In one embodiment, the polymerization temperature is from about 20° C. to about 200° C. In another embodiment, the polymerization temperature is from about 50° C. to about 180° C. In one embodiment, the polymerization pressure is typically from atmospheric pressure to about 100 kg/cm². In another embodiment, the polymerization pressure is typically from about 2 kg/cm² to about 50 kg/cm². The main polymerization may be carried out batchwise, semi-continuously or continuously. The polymerization may also be carried out in two or more stages under different reaction conditions.

The olefin polymer so obtained may be a homopolymer, a random copolymer, a block copolymer or an impact copolymer. The impact copolymer contains an intimate mixture of a polyolefin homopolymer and a polyolefin rubber. Examples of polyolefin rubbers include ethylene propylene rubber (EPR) such as ethylene propylene methylene copolymer rubber (EPM) and ethylene propylene diene methylene terpolymer rubber (EPDM).

The olefin polymer obtained by using the catalyst system has a very small amount of an amorphous polymer component and therefore a small amount of a hydrocarbon-soluble component. Accordingly, a film molded from the resultant polymer has low surface tackiness.

The polyolefin obtained by the polymerization process is excellent in particle size distribution, particle diameter and bulk density, and the copolyolefin obtained has a narrow composition distribution. In an impact copolymer, excellent fluidity, low temperature resistance, and a desired balance between stiffness and elasticity can be obtained.

In one embodiment, propylene and an alpha-olefin having 2 or from about 4 to about 20 carbon atoms are copolymerized in the presence of the catalyst system described above. The catalyst system may be one subjected to the preliminary polymerization described above. In another embodiment, propylene and an ethylene rubber are formed in two reactors coupled in series to form an impact polymer.

The alpha-olefin having 2 carbon atoms is ethylene, and examples of the alpha-olefin having about 4 to about 20 carbon atoms are 1-butene, 1-pentene, 4-methyl-1-pentene, 1-octene, 1-hexene, 3-methyl-1-pentene, 3-methyl-1-butene, 1-decene, vinylcyclohexane, 1-tetradecene, and the like.

In the main polymerization, propylene may be copolymerized with two or more such alpha-olefins. For example, it is possible to copolymerize propylene with ethylene and 1-butene. In one embodiment, propylene is copolymerized with ethylene, 1-butene or ethylene and 1-butene.

Block copolymerization of propylene and another alpha-olefin may be carried out in two stages. The polymerization in a first stage may be the homopolymerization of propylene or the copolymerization of propylene with the other alpha-olefin. In one embodiment, the amount of the monomers polymerized in the first stage is from about 50 to about 95% by weight. In another embodiment, the amount of the monomers polymerized in the first stage is from about 60 to about 90% by weight. In the present application, this first stage polymerization may, as required be carried out in two or more stages under the same or different polymerization conditions.

In one embodiment, the polymerization in a second stage is desirably carried out such that the mole ratio of propylene to the other alpha-olefin(s) is from about 10/90 to about 90/10. In another embodiment, the polymerization in a second stage is desirably carried out such that the mole ratio of propylene to the other alpha-olefin(s) is from about 20/80 to about 80/20. In yet another embodiment, the polymerization in a second stage is desirably carried out such that the mole ratio of propylene to the other alpha-olefin(s) is from about 30/70 to about 70/30. Producing a crystalline polymer or copolymer of another alpha-olefin may be provided in the second polymerization stage.

The propylene copolymer so obtained may be a random copolymer or the above-described block copolymer. This propylene copolymer typically contains from about 7 to about 50 mole % of units derived from the alpha-olefin having 2 or from about 4 to about 20 carbon atoms. In one embodiment, a propylene random copolymer contains from about 7 to about 20 mole % of units derived from the alpha-olefin having 2 or from about 4 to about 20 carbon atoms. In another embodiment, the propylene block copolymer contains from about 10 to about 50 mole % of units derived from the alpha-olefin having 2 or 4-20 carbon atoms.

In another embodiment, copolymers made with the catalyst system contain from about 50% to about 99% by weight poly-alpha-olefins and from about 1% to about 50% by weight comonomers (such as thermoplastic or elastomeric monomers). In another embodiment, copolymers made with the catalyst system contain from about 75% to about 98% by weight poly-alpha-olefins and from about 2% to about 25% by weight comonomers.

It should be understood that where there is no reference to the polyunsaturated compound that can be used, the method of polymerization, the amount of the catalyst system and the polymerization conditions, the same description as the above embodiment are applicable.

The catalysts/methods of the present application can be in some instances lead to the production of poly-alpha-olefins having xylene soluble (XS) from about 0.5% to about 10%. In another embodiment, poly-alpha-olefins having xylene soluble (XS) from about 1.5% to about 8% are produced in accordance with the present disclosure. XS refers to the percent of solid polymer that dissolves into xylene. A low XS % value generally corresponds to a highly isotactic polymer (i.e., higher crystallinity), whereas a high XS % value generally corresponds to a low isotactic polymer.

In one embodiment, the catalyst efficiency (measured as kilogram of polymer produced per gram of catalyst) of the catalyst system of the present disclosure is at least about 30. In another embodiment, the catalyst efficiency of the catalyst system of the present disclosure is at least about 60.

The catalysts/methods of the present application can in some instances lead to the production of poly-alpha-olefins having melt flow indexes (MFI) from about 0.1 to about 100. The MFI is measured according to ASTM standard D1238. In another embodiment, poly-alpha-olefins having an MFI from about 5 to about 30 are produced in accordance with the present disclosure. In one embodiment, an impact polypropylene-ethylenepropylene rubber product has an MFI from about 4 to about 10. In another embodiment, an impact polypropylene-ethylenepropylene rubber product has an MFI from about 5 to about 9. In some instances a relatively high MFI indicates relatively high catalyst efficiency is obtainable.

The catalysts/methods of the present application can in some instances lead to the production of poly-alpha-olefins having bulk densities (BD) of at least about 0.3 cc/g. In another embodiment, poly-alpha-olefins having a BD of at least about 0.4 cc/g are produced in accordance with the present disclosure.

In one embodiment, an impact polypropylene-ethylenepropylene rubber product having a BD of at least about 0.3 cc/g is produced in accordance with the present disclosure. In another embodiment, an impact polypropylene-ethylenepropylene rubber product having a BD of at least about 0.4 cc/g is produced in accordance with the present disclosure.

The catalysts/methods of the present application lead to the production of poly-alpha-olefins having a relatively narrow molecular weight distribution. Polydispersive Index (PI) is strictly connected with the molecular weight distribution of the polymer. PI is calculated as the weight average molecular weight divided by the number average molecular weight, $PI=M_w/M_n$. In one embodiment, the PI of a polypropylene polymer made with the catalyst system is from about 2 to about 12. In another embodiment, the PI of a polypropylene polymer made with the catalyst system is from about 5 to about 11.

The present disclosure can lead to the production of a propylene block copolymer and impact copolymers including polypropylene based impact copolymer having one or more excellent melt-flowability, moldability desirable balance between rigidity and elasticity, good stereospecific control, good control over polymer particle size, shape, size distribution, and molecular weight distribution, and impact strength with a high catalytic efficiency and/or good operability. Employing the catalyst systems containing the olefin polymerization catalyst component according to the present disclosure yields catalysts simultaneously having high catalytic efficiency, and one or more of excellent melt-flowability, extrudability, moldability, rigidity-elasticity and impact strength.

Examples of systems for polymerizing olefins are now described. Referring to FIG. 1, a high level schematic diagram of a system 10 for polymerizing olefins is shown. Inlet 12 is used to introduce into a reactor 14 catalyst system components, olefins, optional comonomers, hydrogen gas, fluid media, pH adjusters, surfactants, and any other additives. Although only one inlet is shown, many often are employed. Reactor 14 is any suitable vehicle that can polymerize olefins. Examples of reactor 14 include a single reactor, a series of two or more reactors, slurry reactors, fixed bed reactors, gas phase reactors, fluidized gas reactors, loop reactors, multizone circulating reactors, and the like. Once polymerization is complete, or as polyolefins are produced, the polymer product is removed from the reactor 14 via outlet 16 which leads to a collector 18. Collector 18 may include downstream processing, such as heating, extrusion, molding, and the like.

Figure 2:
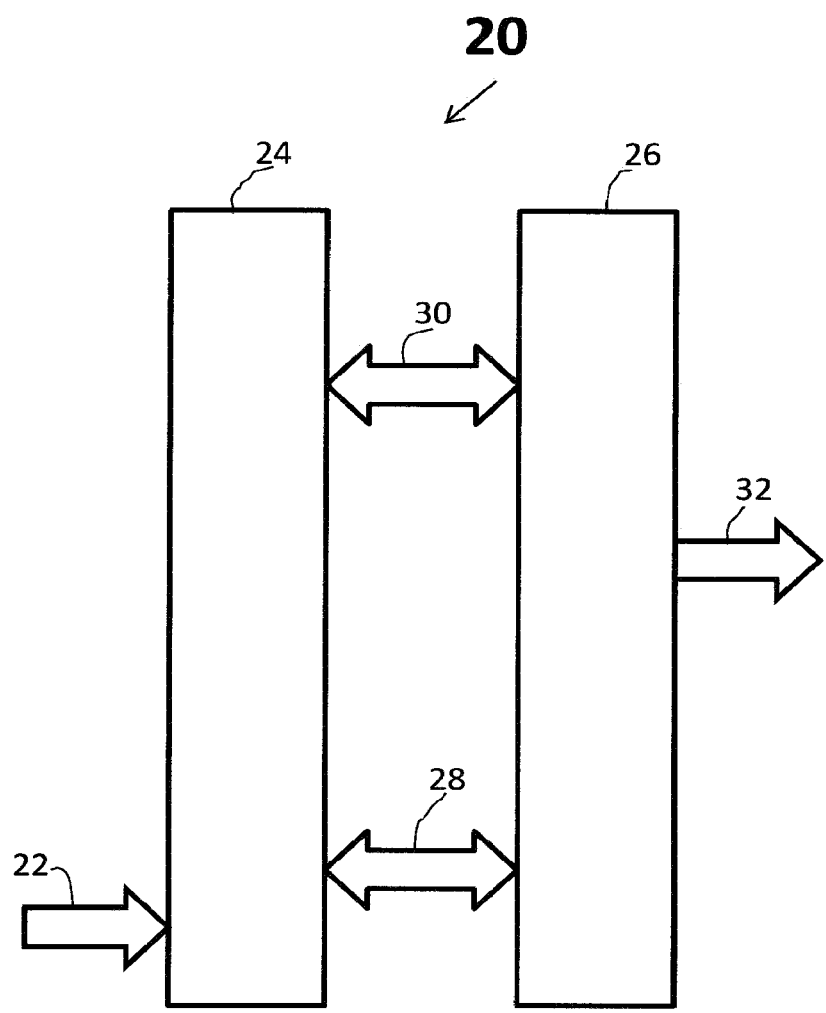
FIG. 2 is a schematic diagram of an olefin polymerization reactor in accordance with another embodiment of this application.
Figure 3:
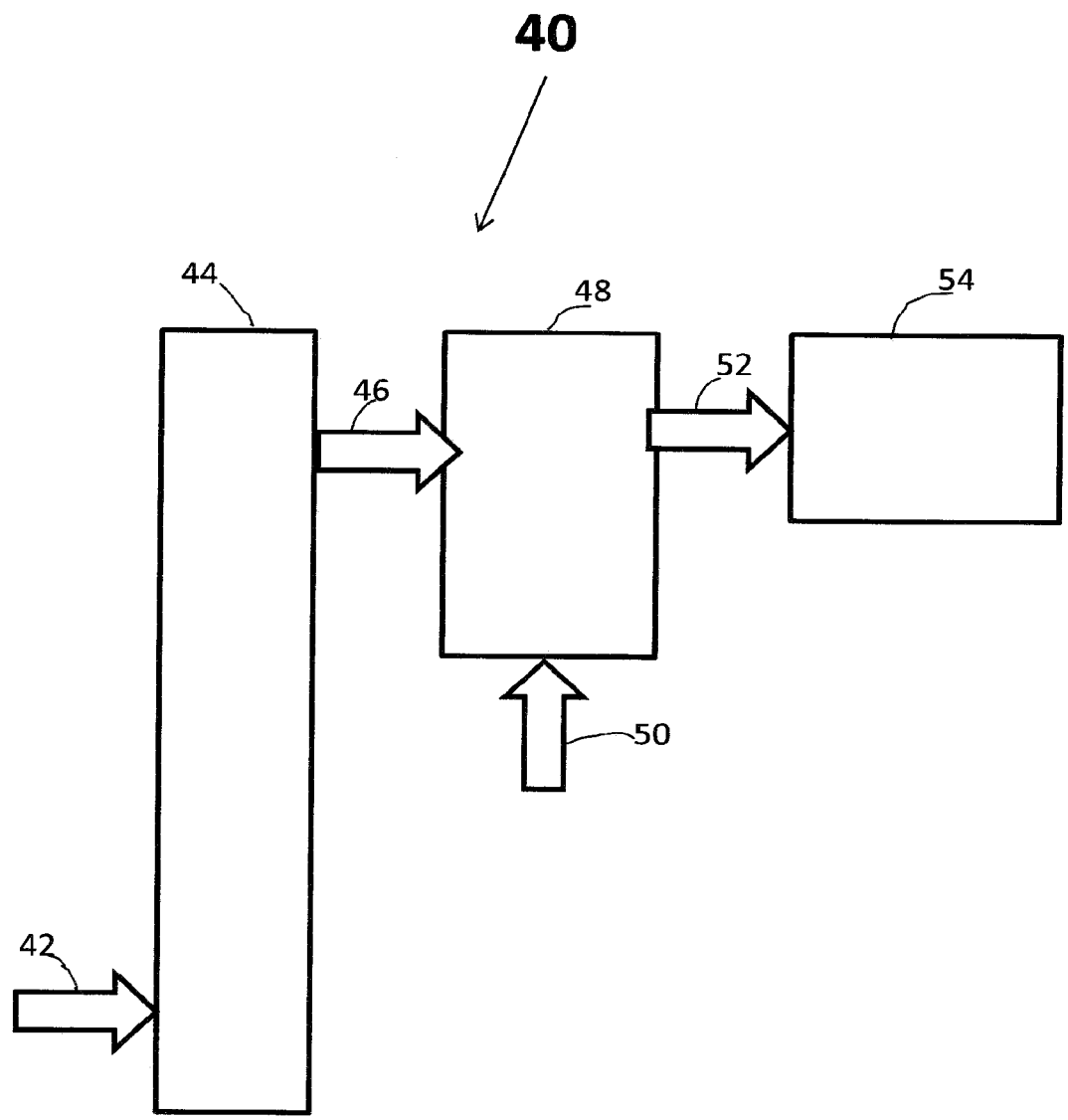
FIG. 3 is a high level schematic diagram of a system for making impact copolymer in accordance with yet another embodiment of this application.

Referring to FIG. 2, a schematic diagram of a multizone circulating reactor 20 that can be employed as the reactor 14 in FIG. 1 or the reactor 44 in FIG. 3 for making polyolefins is shown. The multizone circulating reactor 20 substitutes a series of separate reactors with a single reactor loop that permits different gas phase polymerization conditions in two sides due to use of a liquid barrier. In the multizone circulating reactor 20, a first zone starts out rich in olefin monomers, and optionally one or more comonomers. A second zone is rich in hydrogen gas, and a high velocity gas flow divides the growing resin particles out loosely. The two zones produce resins of different molecular weights and/or monomer compositions. Polymer granules grow as they circulate around the loop, building up alternating layers of each polymer fraction in an onion like fashion. Each polymer particle constitutes an intimate combination of both polymer fractions.

In operation, the polymer particles pass up through the fluidizing gas in an ascending side 24 of the loop and come down through the liquid monomer on a descending side 26. The same or different monomers (and again optionally one or more comonomers) can be added in the two reactor legs. The reactor uses the catalyst system described above.

In the liquid/gas separation zone 30, hydrogen gas is removed to cool and recirculate. Polymer granules are then packed into the top of the descending side 26, where they then descend. Monomers are introduced as liquids in this section. Conditions in the top of the descending side 26 can be varied with different combinations and/or proportions of monomers in successive passes.

Referring to FIG. 3, a high level schematic diagram of another system 40 for polymerizing olefins is shown. This system is ideally suited to make impact polymers. A reactor 44, such as a single reactor, a series of reactors, or a multizone circulating reactor is paired with a gas phase or a fluidized bed reactor 48 downstream containing the catalyst systems described above to make impact copolymers with desirable impact to stiffness balance or greater softness than made with conventional catalyst systems. Inlet 42 is used to introduce into the reactor 44 catalyst system components, olefins, optional comonomers, hydrogen gas, fluid media, pH adjusters, surfactants, and any other additives. Although only one inlet is shown, many often are employed. Through transfer means 46 the polyolefin made in the first reactor 44 is sent to a second reactor 48. Feed 50 is used to introduce catalyst system components, olefins, optional comonomers, fluid media, and any other additives. The second reactor 48 may or may not contain catalyst system components. Again, although only one inlet is shown, many often are employed. Once the second polymerization is complete, or as impact copolymers are produced, the polymer product is removed from the second reactor 48 via outlet 52 which leads to a collector 54. Collector 54 may include downstream processing, such as heating, extrusion, molding, and the like. At least one of the first reactor 44 and the second reactor 48 contains catalyst systems in accordance with the disclosure.

When making an impact copolymer, polypropylene can be formed in the first reactor while an ethylene propylene rubber can be formed in the second reactor. In this polymerization, the ethylene propylene rubber in the second reactor is formed with the matrix (and particularly within the pores) of the polypropylene formed in the first reactor. Consequently, an intimate mixture of an impact copolymer is formed, wherein the polymer product appears as a single polymer product. Such an intimate mixture cannot be made by simply mixing a polypropylene product with an ethylene propylene rubber product.

Although not shown in any of the figures, the systems and reactors can be controlled, optionally with feedback based on continuous or intermittent testing, using a processor equipped with an optional memory and controllers. For example, a processor may be connected to one or more of the reactors, inlets, outlets, testing/measuring systems coupled with the reactors, and the like to monitor and/or control the polymerization process, based on preset data concerning the reactions, and/or based on testing/measuring data generated during a reaction. The controller may control valves, flow rates, the amounts of materials entering the systems, the conditions (temperature, reaction time, pH, etc.) of the reactions, and the like, as instructed by the processor. The processor may contain or be coupled to a memory that contains data concerning various aspects of the polymerization process.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about".

The following examples illustrate the present application. Unless otherwise indicated in the following examples and elsewhere in the specification and claims, all parts and percentages are by weight, all temperatures are in ° C. (degrees Celsius), and pressure is at or near atmospheric pressure.

EXAMPLES

Example 1

3.3 g of MgCl2, 0.8 g phthalic anhydride, 6.41 g epichlorohydrin, 6.70 g tributylphosphate, and 40.92 g toluene were added into a 250 ml reactor under nitrogen. The mixture was heated to 60° C. and agitated at 400 rpm for 2 hours. The mixture was cooled to −30° C., then 65 g $TiCl_4$ were added and the reactor was maintained at −25° C. during the addition. The agitation was reduced to 200 rpm and the reactor was heated to 85° C. in two hours. After that, the agitation was increased to 400 rpm for 30 minutes. Then 3.9 mmol of (D-1)

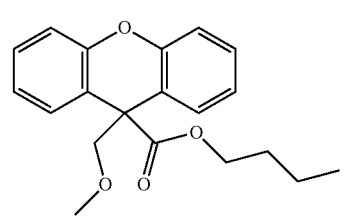

(D-1)

were added and stirred for one hour, then filtered. Then 38 ml toluene and 2.08 mmol (D-1) were added into the reactor and the mixture was heated to 85° C. at 400 rpm and stirred for one hour and filtered. The heat was turned off, and the mixture was washed with 65 ml toluene and filtered. Another 65 ml toluene was added and the mixture was held under nitrogen overnight without stifling. The toluene was removed by filtering, and 66.25 ml of 10% wt $TiCl_4$-toluene were added and the mixture was heated to 95° C. at 400 rpm for one hour and filtered. The previous step was repeated 3 times at 110° C., 400 rpm, and 30 minute each. The final catalyst was washed 4 times with 65 ml hexane and collected as a hexane slurry.

Example 2

Propylene polymerization was performed in a one gallon reactor. The reactor was purged at 100° C. under nitrogen for one hour. At room temperature 1.5 ml of 25 wt % triethyl aluminum in heptane was added into the reactor. Then add 0.94 ml of 0.0768 M solution of cyclohexyl methyl dimethoxy silane followed by 7.0 mg catalyst as 1 wt % hexane slurry into the reactor. The reactor was charged with 4 standard liter $H_2$ followed by 1300 g propylene. The reactor was heated to then be held at 70° C. for one hour. At the end of the hold, the reactor was vented and the polymer was recovered.

Example 3

The following compounds were shown to have the following properties shown in Table 1.

It will now be apparent to those skilled in the art that this specification describes new, useful, and nonobvious catalyst systems including olefin polymerization catalyst components for use in olefin polymerization, methods of making the olefin polymerization catalyst components and the catalyst systems, and methods of polymerizing or copolymerizing alpha-olefins using the catalyst systems. It will also be apparent to those skilled in the art that numerous modifications, variations, substitutes, and equivalents exist for various embodiments of this disclosure that have been described hereinabove. Accordingly, it is expressly intended that all such modifications, variations, substitutions, and equivalents that fall within the spirit and scope of the application, as defined by the appended claims, be embraced thereby.

What is claimed is:

1. An olefin polymerization catalyst component comprising an internal electron donor compound represented by formula (I):

TABLE 1

| Internal Electron Donor Compound(s) | Activity (CE) | % Xylene Soluble (% XS) | Melt Flow Rate (MFR) | Poly-dispersive Index (PI) |
|---|---|---|---|---|
| 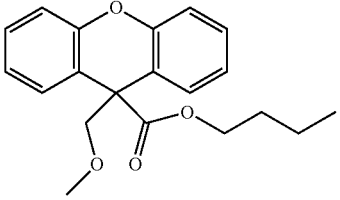 BB1-7 | 52.3 | 5.85 | 8.3 | 5.21 |
| 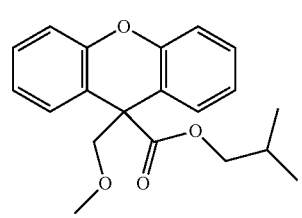 BB1-8 | 47.1 | 5.73 | 9.5 | N/A |
| 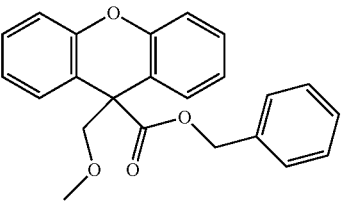 BB1-9 | 25.1 | 5.88 | 14.8 | N/A |

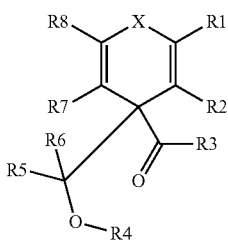

wherein:

X is O, S, NR$^a$, PR$^b$, or POOR$^c$,

R$^a$ is hydrogen, halogen, a carbonyl hydrocarbon, a linear or branched unsaturated or saturated alkyl hydrocarbon, or an unsubstituted or halogen-substituted moiety selected from the group consisting of a cyclic, an aromatic, and an aliphatic hydrocarbon, R$^b$ is hydrogen, halogen, a carbonyl hydrocarbon, a linear or branched unsaturated or saturated alkyl hydrocarbon, a linear or branched unsaturated or saturated alkoxy hydrocarbon, or an unsubstituted or halogen-substituted moiety selected from the group consisting of a cyclic, an aromatic, and an aliphatic hydrocarbon, R$^c$ is hydrogen, a carbonyl hydrocarbon, a linear or branched unsaturated or saturated alkyl hydrocarbon, or an unsubstituted or halogen-substituted moiety selected from the group consisting of a cyclic, an aromatic, and an aliphatic hydrocarbon, and R1-R8 are identical or different and are hydrogen, halogen, a linear or branched unsaturated or saturated C1-C30 alkyl, or an unsubstituted or halogen-substituted moiety selected from the group consisting of C5-C30 substituted or unsubstituted 5-or 6-membered aliphatic and aromatic hydrocarbon rings.

2. The olefin polymerization catalyst component of claim 1, wherein R1 and R2 and/or R7 and R8 form a 5-or 6-membered aliphatic or aromatic hydrocarbon ring optionally substituted with halogen; and R3 is linear or branched unsaturated or saturated C$_1$-C$_{12}$ alkyl or R3 is linear or branched C$_1$-C$_{12}$ alkoxy.

3. The olefin polymerization catalyst component of claim 1, wherein X is O.

4. The olefin polymerization catalyst component of claim 1, wherein the internal electron donor compound is (D-1) shown below

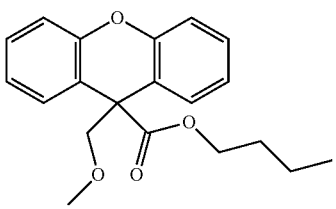

5. A catalyst system for polymerization of an olefin comprising:
a) the olefin polymerization catalyst component of claim 1 further comprising a titanium halide and/or a magnesium halide;
b) an organoaluminum compound; and
c) optionally an external electron donor.

6. The catalyst system of claim 5, wherein the magnesium halide is magnesium chloride and the titanium halide is TiCl$_4$ or TiCl$_3$.

7. The catalyst system of claim 5, wherein the organoaluminum compound is an alkyl-aluminum compound.

8. The catalyst system of claim 7, wherein the alkyl-aluminum compound is a trialkyl aluminum compound.

9. The catalyst system of claim 8, wherein the trialkyl aluminum compound is selected from the group consisting of triethylaluminum, triisobutylaluminum, and tri-n-octyl-aluminum, and combinations thereof.

10. The catalyst system of claim 5 further comprising esters, phthalate compounds, ketones, and/or ethers.

11. A process for polymerizing or copolymerizing an olefin, the process comprising
(a) providing a catalyst system of claim 5;
(b) polymerizing or copolymerizing the olefin in a presence of the catalyst system to form a polymer or a copolymer; and
(c) recovering the polymer or the copolymer.

12. The process of claim 11, wherein the olefin is selected from the group consisting of ethylene, propylene, 1-butylene, 4-methyl-1-pentente, 1-hexene, 1-octene, and mixtures thereof.

13. A catalyst system for polymerization of an olefin, the catalyst system comprising a catalyst component comprising an internal electron donor compound represented by formula (I):

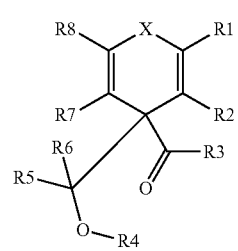

wherein:

X is O, S, NR$^a$, PR$^b$, or POOR$^c$,

R$^a$ is hydrogen, halogen, a carbonyl hydrocarbon, a linear or branched unsaturated or saturated alkyl hydrocarbon, or an unsubstituted or halogen-substituted moiety selected from the group consisting of a cyclic, an aromatic, and an aliphatic hydrocarbon, R$^b$ is hydrogen, halogen, a carbonyl hydrocarbon, a linear or branched unsaturated or saturated alkyl hydrocarbon, a linear or branched unsaturated or saturated alkoxy hydrocarbon, or an unsubstituted or halogen-substituted moiety selected from the group consisting of a cyclic, an aromatic, and an aliphatic hydrocarbon, R$^c$ is hydrogen, a carbonyl hydrocarbon, a linear or branched unsaturated or saturated alkyl hydrocarbon, or an unsubstituted or halogen-substituted moiety selected from the group consisting of a cyclic, an aromatic, and an aliphatic hydrocarbon, and R1-R8 are identical or different and are hydrogen, halogen, a linear or branched unsaturated or saturated C1-C30 alkyl, or an unsubstituted or halogen-substituted moiety selected from the group consisting of C5-C30 substituted or unsubstituted 5-or 6-membered aliphatic and aromatic hydrocarbon rings.

14. The catalyst system of claim 13, wherein X is O; R1 and R2 and/or R7 and R8 form a 5-or 6-membered hydrocarbon ring optionally substituted with halogen; and R3 is linear or branched unsaturated or saturated $C_1$-$C_{12}$ alkyl or R3 is linear or branched $C_1$-$C_{12}$ alkoxy.

15. A catalyst system for use in olefinic polymerization, the catalyst system comprising:
the olefin polymerization catalyst component of claim 1;
an organoaluminum compound; and
an organosilicon compound.

16. The catalyst system of claim 15, wherein the organoaluminum compound is an alkyl-aluminum compound.

17. The catalyst system of claim 16, wherein the alkyl-aluminum compound is a trialkyl aluminum compound.

18. The catalyst system of claim 17, wherein the trialkyl aluminum compound is selected from the group consisting of triethylaluminum, triisobutylaluminum, and tri-n-octyl-aluminum, and combinations thereof.

19. The catalyst system of claim 15, wherein the organosilicon compound is represented by chemical formula (II):

$$R_nSi(OR')_{4-n} \quad \text{(II)}$$

wherein each R and R' independently represent a hydrocarbon group, and n is an integer from 0 to 3.

20. The catalyst system of claim 15, wherein the organosilicon compound is represented by chemical formula (III):

$$SiRR'_m(OR'')_{3-m} \quad \text{(III)}$$

wherein R represents a cyclic hydrocarbon or substituted cyclic hydrocarbon group, wherein each R' and R" independently represent a hydrocarbon group, and wherein m is an integer from 0 to 2.

21. A process of polymerizing or copolymerizing an olefin monomer, the process comprising:
(i) providing the catalyst system of claim 15;
(ii) polymerizing or copolymerizing the olefin monomer in the presence of the catalyst system to form a polymer or a copolymer; and
(iii) recovering the polymer or the copolymer.

22. The process of claim 21, wherein the olefin monomer is selected from the group consisting of ethylene, propylene, 1-butylene, 4-methyl-1-pentene, 1-hexane, 1-octene, and combinations thereof.

* * * * *

UNITED STATES PATENT AND TRADEMARK OFFICE
CERTIFICATE OF CORRECTION

| | | |
|---|---|---|
| PATENT NO. | : 9,637,575 B2 | Page 1 of 1 |
| APPLICATION NO. | : 14/588379 | |
| DATED | : May 2, 2017 | |
| INVENTOR(S) | : Binh Thanh Nguyen and Jonas Alves Fernandes | |

It is certified that error appears in the above-identified patent and that said Letters Patent is hereby corrected as shown below:

In the Claims

Claim 12, Column 24, Line 24:
Delete "4-methyl-1-pentente" and insert --4-methyl-1-pentene-- therefor.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*